United States Patent
Flower et al.

(10) Patent No.: US 12,016,534 B2
(45) Date of Patent: Jun. 25, 2024

(54) LIGHTED CANNULA SYSTEM

(71) Applicant: Rebound Therapeutics Corporation, Irvine, CA (US)

(72) Inventors: Robert J. Flower, Irvine, CA (US); Mark J. Zechmeister, Irvine, CA (US); Lindsay Lam, Irvine, CA (US); Todd D. McIntyre, Irvine, CA (US); Peter G. Davis, Irvine, CA (US); Ravut Chhit, Irvine, CA (US)

(73) Assignee: Rebound Therapeutics Corporation, Irvine, CA (US)

( * ) Notice: Subject to any disclaimer, the term of this patent is extended or adjusted under 35 U.S.C. 154(b) by 652 days.

(21) Appl. No.: 16/785,187

(22) Filed: Feb. 7, 2020

(65) Prior Publication Data

US 2020/0253464 A1     Aug. 13, 2020

Related U.S. Application Data

(60) Provisional application No. 62/803,276, filed on Feb. 8, 2019.

(51) Int. Cl.
*A61B 1/06* (2006.01)
*A61B 1/04* (2006.01)
(Continued)

(52) U.S. Cl.
CPC ............ *A61B 1/0669* (2013.01); *A61B 1/042* (2013.01); *A61B 17/3423* (2013.01);
(Continued)

(58) Field of Classification Search
CPC ....... A61B 1/06; A61B 1/0607; A61B 1/0615; A61B 1/0661; A61B 1/0669;
(Continued)

(56) References Cited

U.S. PATENT DOCUMENTS

| | | | | |
|---|---|---|---|---|
| 3,146,775 A | * | 9/1964 | Moore | A61B 1/227 385/115 |
| 5,325,458 A | * | 6/1994 | Morrow | G02B 6/032 385/124 |

(Continued)

FOREIGN PATENT DOCUMENTS

| | | |
|---|---|---|
| JP | 2002518340 | 6/2002 |
| JP | 2008515554 | 5/2008 |

(Continued)

OTHER PUBLICATIONS

International Search Report and Written Opinion dated Jun. 10, 2020 from IA PCT/US2020/017276.

(Continued)

*Primary Examiner* — Ryan N Henderson
(74) *Attorney, Agent, or Firm* — Crockett & Crockett, PC; K. David Crockett, Esq.

(57) ABSTRACT

A cannula suitable for use in minimally invasive surgery is improved with a highly polished and very smooth luminal wall and/or LED's or other light sources focused at particular angles relative to the axis of the cannula. The devices provide for improved lighting and/or reduced lighting requirements for cannulas used for minimally invasive surgery.

18 Claims, 4 Drawing Sheets

(51) Int. Cl.
*A61B 1/313* (2006.01)
*A61B 17/34* (2006.01)

(52) U.S. Cl.
CPC .......... *A61B 1/0607* (2013.01); *A61B 1/0684* (2013.01); *A61B 1/313* (2013.01)

(58) Field of Classification Search
CPC .............. A61B 1/0684; A61B 90/30; A61B 2090/0454; A61B 17/3421; A61B 17/3423; A61B 2090/309; A61B 1/042
See application file for complete search history.

(56) References Cited

U.S. PATENT DOCUMENTS

| | | | | |
|---|---|---|---|---|
| 5,729,646 | A * | 3/1998 | Miyagi | G02B 6/102 385/125 |
| 5,953,477 | A * | 9/1999 | Wach | G02B 6/4203 385/115 |
| 6,141,476 | A * | 10/2000 | Matsuura | G02B 6/032 385/125 |
| 6,432,101 | B1 * | 8/2002 | Weber | A61B 18/24 606/2 |
| 6,676,264 | B1 * | 1/2004 | Mima | G02B 27/0994 385/125 |
| 7,556,601 | B2 * | 7/2009 | Branch | A61B 90/36 600/245 |
| 7,783,346 | B2 * | 8/2010 | Smith | A61B 17/3421 606/4 |
| 7,874,982 | B2 * | 1/2011 | Selover | A61B 17/3421 600/199 |
| 7,901,353 | B2 * | 3/2011 | Vayser | A61B 1/3132 606/17 |
| 8,409,088 | B2 * | 4/2013 | Grey | A61B 17/02 600/212 |
| 8,430,813 | B2 * | 4/2013 | Selover | A61B 1/0607 600/245 |
| 8,480,566 | B2 * | 7/2013 | Farr | A61B 1/00096 600/129 |
| 9,005,118 | B2 * | 4/2015 | Selover | A61B 17/02 600/245 |
| 9,161,820 | B2 * | 10/2015 | Mark | A61M 39/06 |
| 9,186,175 | B2 * | 11/2015 | Mark | A61B 90/50 |
| 9,918,802 | B2 * | 3/2018 | Coppersmith | F21V 29/70 |
| 10,068,173 | B2 * | 9/2018 | Vayser | G09B 19/003 |
| 10,105,042 | B2 * | 10/2018 | Davis | A61B 90/361 |
| 10,245,071 | B2 * | 4/2019 | Wood | A61B 17/3423 |
| 10,502,939 | B2 * | 12/2019 | Senn | G02B 27/0977 |
| 10,729,511 | B2 * | 8/2020 | Vayser | A61B 1/00135 |
| 11,173,008 | B2 * | 11/2021 | Mirsepassi | A61B 1/07 |
| 2004/0143167 | A1 * | 7/2004 | Branch | A61B 90/30 600/212 |
| 2004/0143169 | A1 * | 7/2004 | Branch | A61B 90/36 600/245 |
| 2005/0027168 | A1 * | 2/2005 | Strom | A61B 1/227 600/200 |
| 2005/0177168 | A1 * | 8/2005 | Brunnett | A61B 17/1624 606/80 |
| 2005/0234296 | A1 | 10/2005 | Saadat et al. | |
| 2006/0041193 | A1 * | 2/2006 | Wright | A61B 1/0684 600/179 |
| 2006/0069314 | A1 * | 3/2006 | Farr | A61B 1/0653 600/179 |
| 2006/0224045 | A1 * | 10/2006 | Whipple | A61B 90/30 600/245 |
| 2006/0268570 | A1 * | 11/2006 | Vayser | A61B 17/3421 362/572 |
| 2007/0100210 | A1 * | 5/2007 | Selover | A61B 17/02 600/199 |
| 2007/0100211 | A1 * | 5/2007 | Selover | A61B 17/02 600/199 |
| 2007/0179430 | A1 * | 8/2007 | Smith | A61F 9/00736 604/20 |
| 2007/0208226 | A1 * | 9/2007 | Grey | A61B 1/06 600/212 |
| 2007/0276191 | A1 * | 11/2007 | Selover | A61B 17/3421 606/14 |
| 2009/0036744 | A1 * | 2/2009 | Vayser | A61B 1/00135 600/245 |
| 2009/0163897 | A1 * | 6/2009 | Skinner | A61F 9/00745 606/4 |
| 2010/0114118 | A1 * | 5/2010 | Harris | A61B 17/32053 606/133 |
| 2011/0021882 | A1 * | 1/2011 | Selover | A61B 17/3423 600/245 |
| 2011/0112376 | A1 * | 5/2011 | Vayser | A61M 1/84 600/249 |
| 2012/0041268 | A1 * | 2/2012 | Grey | A61B 1/267 600/199 |
| 2012/0253375 | A1 * | 10/2012 | Mark | A61B 1/00165 606/185 |
| 2013/0012783 | A1 * | 1/2013 | Vayser | A61B 1/0017 600/249 |
| 2013/0158488 | A1 * | 6/2013 | Weaver | A61L 29/14 427/2.3 |
| 2013/0158517 | A1 * | 6/2013 | Bouchard | A61L 29/085 604/533 |
| 2013/0158518 | A1 * | 6/2013 | Li | A61L 29/049 604/533 |
| 2013/0204095 | A1 * | 8/2013 | Mark | A61B 17/0218 600/249 |
| 2013/0267786 | A1 * | 10/2013 | Vayser | A61B 1/32 600/213 |
| 2014/0052108 | A1 * | 2/2014 | De Kock | B29C 48/154 604/528 |
| 2014/0088371 | A1 * | 3/2014 | Vayser | A61B 1/0017 600/249 |
| 2014/0316206 | A1 * | 10/2014 | Vasan | A61B 1/00105 600/199 |
| 2015/0025369 | A1 * | 1/2015 | Bhagavatula | A61B 5/0084 29/527.1 |
| 2015/0080896 | A1 * | 3/2015 | To | A61B 17/32001 606/79 |
| 2015/0313630 | A1 * | 11/2015 | Gasparyan | A61M 25/0105 604/117 |
| 2016/0015467 | A1 * | 1/2016 | Vayser | G02B 1/048 600/245 |
| 2016/0235893 | A1 * | 8/2016 | Lucchino | A61L 29/18 |
| 2016/0256234 | A1 * | 9/2016 | Coppersmith | F21V 23/001 |
| 2016/0296744 | A1 | 10/2016 | Chen et al. | |
| 2016/0367279 | A1 * | 12/2016 | Glennon | A61B 1/00082 |
| 2017/0203065 | A1 * | 7/2017 | Fuhrman | A61M 16/0402 |
| 2017/0252121 | A1 * | 9/2017 | Diao | B29C 65/14 |
| 2017/0265734 | A1 * | 9/2017 | Vayser | A61B 1/317 |
| 2017/0332887 | A1 * | 11/2017 | Davis | A61B 5/1473 |
| 2018/0085141 | A1 * | 3/2018 | Wood | A61B 90/30 |
| 2018/0161024 | A1 * | 6/2018 | Davis | A61B 1/00 |
| 2018/0364464 | A1 * | 12/2018 | Senn | G02B 19/0019 |
| 2019/0307527 | A1 * | 10/2019 | Grueebler | A61B 17/3421 |
| 2020/0253464 | A1 * | 8/2020 | Flower | A61B 1/042 |
| 2021/0361157 | A1 * | 11/2021 | Tesar | G02B 21/0012 |
| 2022/0257092 | A1 * | 8/2022 | Ng | A61B 1/00071 |

FOREIGN PATENT DOCUMENTS

| | | | |
|---|---|---|---|
| JP | 2012120615 | 6/2012 | |
| JP | 5196711 B2 * | 5/2013 | ....... H01L 2924/151 |
| JP | 201738946 | 2/2017 | |
| WO | WO2015101624 | 7/2015 | |
| WO | WO2018035366 | 2/2018 | |

OTHER PUBLICATIONS

Extended European Search Report dated Aug. 23, 2022 from European Patent Application No. 20752885.2.

(56) References Cited

OTHER PUBLICATIONS

Notification of Reasons for Refusal dated Dec. 5, 2023 from Japanese Patent Application No. 2021-544202.

* cited by examiner

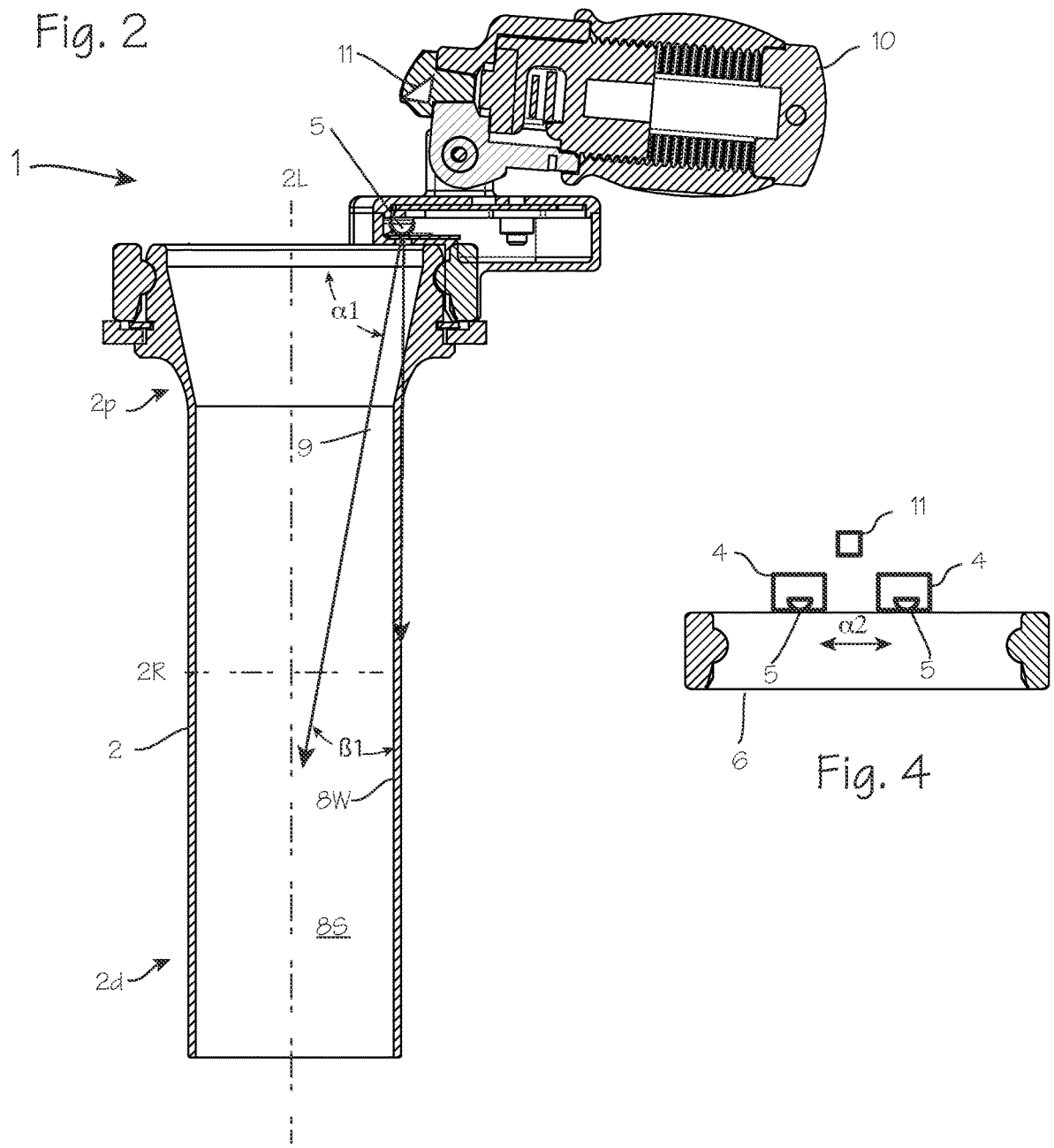

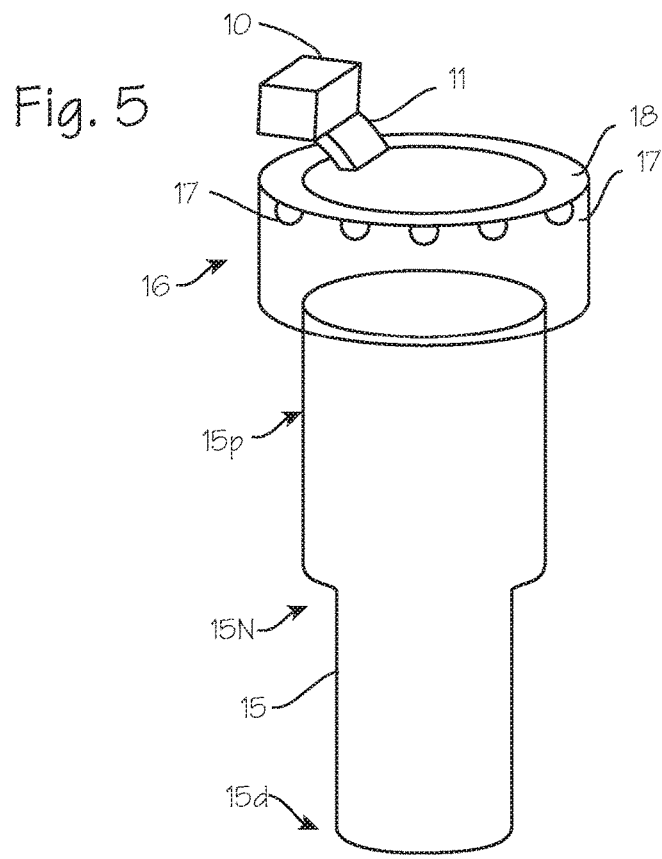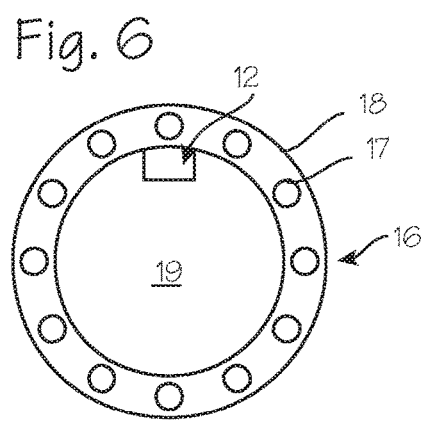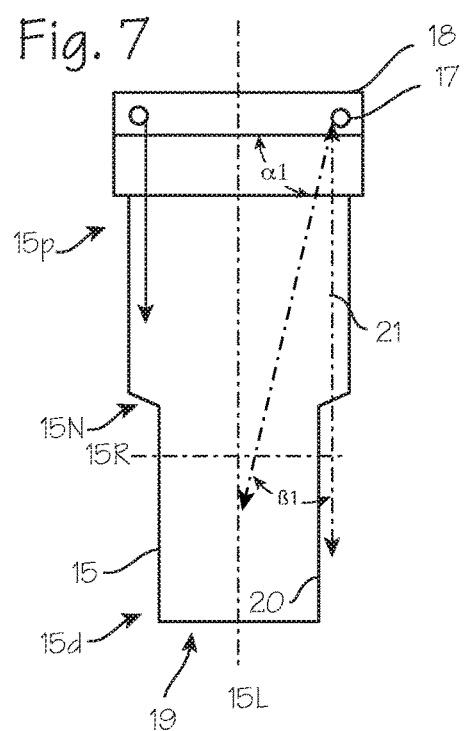

LIGHTED CANNULA SYSTEM

FIELD OF THE INVENTIONS

The inventions described below relate to the field of minimally invasive brain or spine surgery.

BACKGROUND

U.S. Pat. No. 10,172,525 discloses a cannula and proximally mounted camera system for improved visualization of the brain during minimally invasive surgery. The system includes a cannula with a camera mounted on the proximal end of the cannula with a view into the cannula lumen and the tissue within and below the lumen, along with a prism, reflector or other suitable optical element oriented between the camera and the lumen of the cannula to afford the camera a view into the cannula while minimizing obstruction of the lumen. Lighting disclosed in this patent included lights in the cannula to illuminate the distal end of the cannula or tissue near the distal end of the cannula, or light sources provided outside the assembly, or from lights mounted on the proximal end of the cannula.

SUMMARY

The devices and methods describe below provide for improved lighting and/or reduced lighting requirements for cannulas used for minimally invasive surgery. A cannula suitable for use in minimally invasive surgery is improved with a highly polished and very smooth luminal wall and/or LED's or other light sources focused at particular angles relative to the axis of the cannula.

BRIEF DESCRIPTION OF THE DRAWINGS

FIGS. 1 through 4 illustrate a lighted cannula system.

FIGS. 5 through 7 illustrate a lighted cannula system with an cannula tube of non-uniform diameter.

DETAILED DESCRIPTION OF THE INVENTIONS

Figure 1:
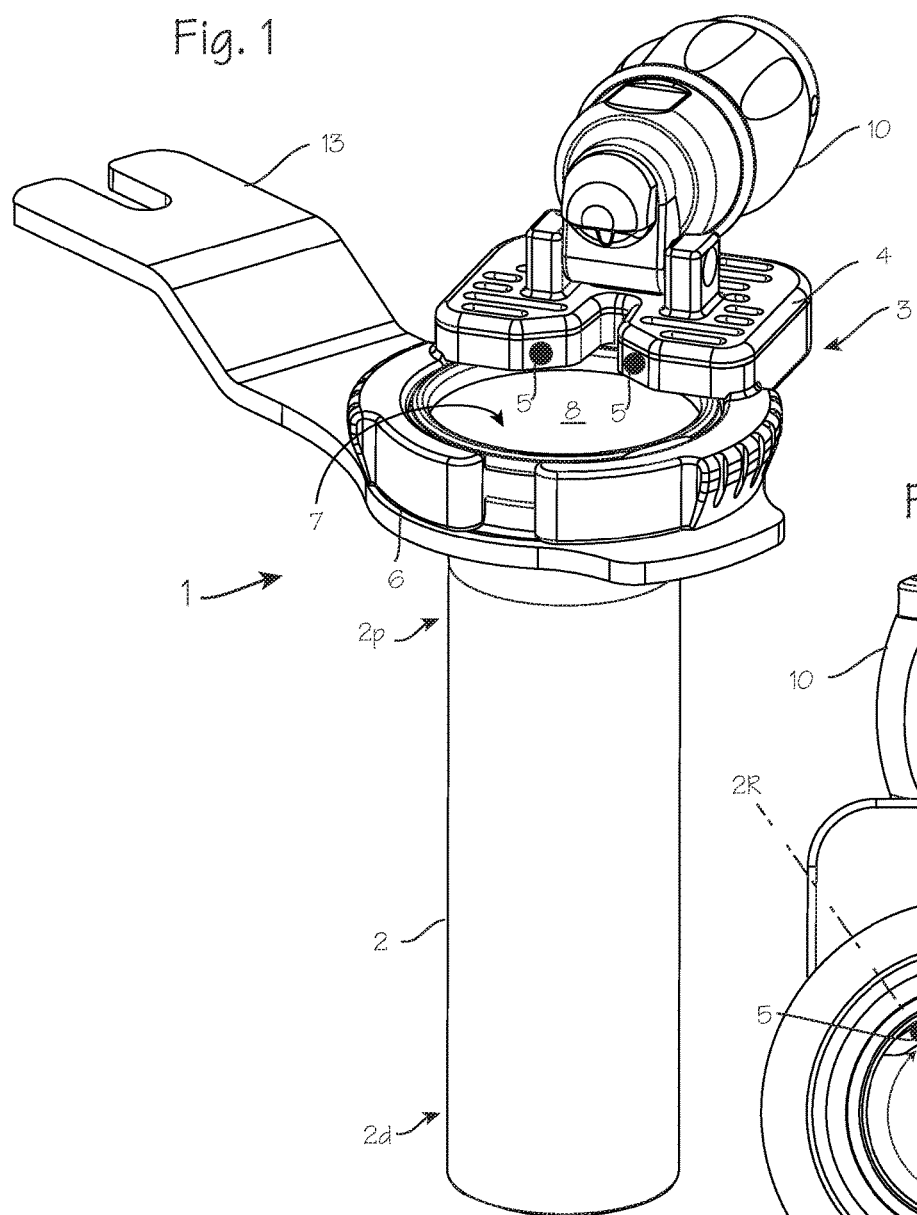

FIG. 1 illustrates a cannula system 1 for accessing a target site in the body of a patient. The cannula system comprises a cannula tube 2 and a lighting assembly 3 disposed proximate the proximal end 2p of the cannula tube. The lighting assembly 3 comprises a housing 4 with a number of light sources 5 (LED's, incandescent bulbs, etc.). The lighting assembly may be mounted on a ring, or partial ring 6 as illustrated, and may be permanently fixed or releasably attachable to the proximal end 2p of the cannula tube, through releasable attachment means such as a C-ring expandable to engage a groove in the proximal end outer surface, or with an annular snap ring, or with screw threads or other easily attachable and detachable mechanisms. The lighting assembly may instead be directly fixed to the proximal end of the cannula tube or fixed on the ring 18 which in turn is fixed to the cannula tube (as shown in FIG. 5 through 8). The cannula tube is characterized by a distal end 2d and a proximal end 2p, and a lumen 7 extending from the proximal end to the distal end, a central longitudinal axis 2L defined by the lumen, and a luminal surface 8S on the inner wall 8W of the cannula tube (FIG. 2). The cannula tube most conveniently has a circular radial cross section, but the radial cross section may be varied to provide for access to particular surgical sites. The cannula tube may consist of an opaque material, non-transmissive to visible light, such as metal, or it may comprise an opaque construction including a luminal surface comprising an opaque material which is non-transmissive to visible light in a cannula tube of transmissive or non-transmissive material (for example, an acrylic tube with a metallic coating). FIG. 2 shows, for example, a cannula tube 2 comprising a material which is transmissive to visible light with a luminal surface 8S comprising a material which is non-transmissive to visible light.

The lighting assembly 3 is disposed proximate the proximal end of the cannula tube, and is configured to hold light 5 proximal to the proximal opening of the cannula tube (this is preferable, but the lights may extend slightly distally into the lumen) to project light into the lumen of the cannula tube. The cannula tube may consist of an opaque material, non-transmissive to visible light, and is preferably made of metal such as stainless steel or aluminum.

The effectiveness of the lighting is preferably enhanced by providing a very smooth surface on the inner wall of the cannula tube. Preferably, the luminal surface is highly polished/smooth with an Average Roughness of 8 micro-inches or smoother ($8^{-6}$ inches, equivalent to Ra (um) 0.2 (0.2 microns), USA #8 finish, Japan Buff #300, or ISO N4 or smoother), to enhance the transmission of light from the proximal end of the cannula to the distal end of the cannula and a target site beyond the distal end of the cannula. The lights of FIG. 1 may have a total output of 200 to 700 lumens, which, in combination with the smooth luminal surface, will provide in ample light at a surgical workspace at the distal end of the cannula tube. Combinations of slightly rougher surfaces with higher power lights may be used. The luminal surface may be provided in a Average Roughness in the range of 9 to 32 micro-inches (between 0.22 to 0.81 micrometers, ISO N5 or N6 finish, #6 or #7 finish (roughly), Japan Buff #100 or smoother) and the lights may be chosen to provide additional lumens, in the higher end of the range. Alternatively, the luminal surface may be provided in a Average Roughness in the range of 33 to 63 micro-inches (0.82 to 1.6 micrometers, ISO N7 finish, USA #3 or #4 finish) and the lights may be chosen to provide additional lumens, in the higher end of the range.

As illustrated in FIG. 2, the light 5 are characterized by a main beam axis 9, which may be directed at an angle $\alpha_1$ of 70° to 85°, though preferably about 80° downward (distally) from the radial axis 2R, or, comparably, directed at an angle $\beta_1$ of 5° to 15°, and preferably about 10°, inward relative to the long axis 2L of the cannula tube, directed distally, in this embodiment where the cannula has a distal portion with a straight inner bore (of consistent diameter throughout the length of the distal portion) and a proximal conical section with a conical bore which is larger than the diameter of the straight inner bore at the proximal end of the proximal conical section and necks down to match the diameter of the straight inner bore of the straight distal portion.

As illustrated in FIG. 2, the lights are characterized by a main beam axis 9, which may be directed at an angle $\alpha_1$ of 80° from the radial axis 2R, directed distally, or at an angle $\beta_1$ of 10° relative to the luminal surface of the cannula tube (toward the center of the lumen).

Though FIGS. 1 and 2 illustrate the system with a cannula tube having a conical lumen in a proximal portion of the cannula tube, the cannula tube may be isodiametric throughout its length, having a consistent or uniform inner diameter and straight luminal walls from the proximal end to the distal end, without a conical portion or a neckdown portion.

Figure 3:
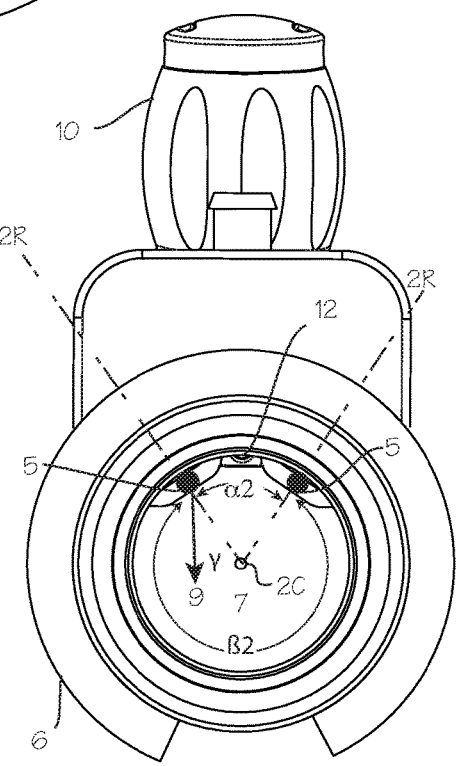

FIG. 3 is a view of the cannula system from the bottom, or distal end of the cannula tube. As shown in this Figure, the beam axis 9 may be aimed to intersect the central axis 2C of the cannula tube, or the beam axis may be aimed at an angle γ from the radian 2R (the line between the LED and the central axis 2C, or, along a chord of the circle defined by the cannula tube). This angle is preferably in the range of about 10 to 30°. As shown in FIGS. 3 and 4, the light source may consist of only two LED's disposed over (proximal to) the proximal end of the cannula tube, either directly or on the ring 6 and separated by a first arc $\alpha_2$ of 50° to 70°, and preferably about 60° as shown in FIG. 3 (or, conversely, the second arc $\beta_2$ of 290° to 310°, and preferably about 300° as shown in FIG. 3). The light source may consist of two pairs of closely spaced lights, with the pairs similarly separated. Preferably, the lights and any associated lenses are disposed proximal to the proximal opening of the cannula tube without extending distally into the lumen. The proximal end of the cannula tube has an inner bore/lumen that is conical, with a proximal opening slightly larger than the diameter of the distal portion of the cannular tube.

As shown in FIG. 1, the cannula system may include a camera assembly 10 secured to the proximal end of the cannula, with a portion of the camera assembly overhanging the lumen and extending into a cylindrical space defined by the lumen of the cannula tube. The camera assembly has a distal-most optical surface, which may be a distal surface of an objective lens or a prism (the prism 11 is shown in FIG. 2, and the distal-most optical surface 12 is visible in the distal view of FIG. 3), and the distal-most optical surface is disposed proximate the proximal end of the cannula tube. The objective lens or prism may be the portion of the camera assembly overhanging the lumen. The distal-most optical surface of the camera system is spaced proximally from the proximal end of the cannula tube in the illustration, but may be placed a short distance distal to the very proximal edge of the cannula tube (without extending to the distal end of the cannula tube). Also as shown in FIG. 1, the cannula system can include a tab 13 for securing the cannula to a table-fixed flex arm. As illustrated in FIGS. 3 and 4, the distal most optical surface of the camera assembly is disposed between the lights, in the smaller arc $\alpha_2$ separating the two lights. A gap in the housing, between the two lights (or two pairs of lights), provides an unobstructed sight-line between the distal-most optical surface and the workspace at the distal end of the cannula tube, and the distal most optical surface of the camera assembly is disposed within this gap or proximal to the gap.

FIG. 5 illustrates a second version of the cannula system for accessing a target site in the body of a patient. The cannula system 14 of FIG. 5 comprises a cannula tube 15 and a lighting assembly 16 disposed proximate the proximal end of the cannula tube. The lighting assembly 16 comprises a number of lights 17 (LED's, incandescent bulbs, etc.) mounted on a ring 18 as illustrated (though a partial ring may be used, or the ring may be omitted), and may be permanently fixed or releasably attachable to the proximal end of the cannula tube, through releasable attachment means such as an annular snap ring, a threaded fitting (or a C-ring expandable to engage a groove in the proximal end outer surface). The cannula tube is characterized by a distal end 15d and a proximal end 15p, and a lumen 19 extending from the proximal end to the distal end, a central longitudinal axis 15L defined by the lumen, and a luminal surface 20 on an inner wall of the cannula tube. The inner diameter of the cannula tube proximal end 15p is longitudinally isodiametric (straight-walled, and not conical as in FIG. 2), and the inner diameter of the cannula tube distal end 15d is longitudinally isodiametric, and the inner diameter of the cannula tube distal end is smaller than the inner diameter of that cannula tube proximal end, and the cannula tube proximal end 15p and cannula tube distal end 15d are joined by a neck-down portion 15N of the cannula tube.

Similar to the construction described in relation to FIGS. 1 through 3, the lighting assembly 16 of FIG. 5 is disposed proximate the proximal end of the cannula tube, and is configured to project light into the lumen of the cannula tube. The cannula tube may consist of an opaque material, non-transmissive to visible light, again preferably metal such as stainless steel or aluminum. The luminal surface is highly polished/smooth with a Average Roughness less that 8 micro-inches, to enhance the transmission of light from the proximal end of the cannula to the distal end of the cannula and a target site beyond the distal end of the cannula. The lights of FIG. 5 may have a total output of 1500 to 2500 lumens, which, in combination with the smooth luminal surface, will provide in ample light at a surgical workspace at the distal end of the cannula tube. As with the cannula tube of FIG. 1, the lights may be chosen to provide additional lumens, in the higher end of the range, with luminal walls of Average Roughness within the range of 9 to 32 micro-inches or in the range of 33 to 63 micro-inches.

As shown in FIG. 6, the lighting assembly 16 may comprise a plurality of LED's 17 disposed on the proximal end of the cannula tube, either directly fixed to the proximal end of the cannula tube or fixed on the ring 18 which in turn is fixed to the cannula tube. The ring 18 may be permanently fixed or releasably attachable to the proximal end 15p of the cannula tube, through releasable attachment means such as a C-ring expandable to engage a groove in the proximal end outer surface, or with an annular snap ring, or with screw threads or other easily attachable and detachable mechanisms.

As shown in the cross section of FIG. 7, the lights 17 are characterized by a main beam axis 21, which may be directed parallel to the straight side wall or the portion of the luminal surface on the inner wall of the proximal end of the cannula tube (that is, the beam axes of each LED may be parallel to a portion of the luminal surface on an inner wall of the cannula). Alternatively, as in the systems of FIGS. 1 and 2, the main beam axis 21 may also be directed at an angle $\alpha_1$ of 70° to 85°, though preferably about 80° downward (distally) from the radial axis 2R, or, comparably, directed at an angle $\beta_1$ of 5° to 15°, and preferably about 10° relative to the luminal surface of the cannula tube (toward the center of the lumen).

The cannula system of FIG. 5 may include a camera assembly 10 secured to the proximal end of the cannula, with a portion of the camera assembly overhanging the lumen and extending into a cylindrical space defined by the lumen of the cannula tube. The camera assembly has a distal-most optical surface, which may be a distal surface of an objective lens or a prism, and the distal-most optical surface is disposed proximate the proximal end of the cannula tube, the objective lens or prism may be the portion of the camera assembly overhanging the lumen. The distal-most optical surface of the camera system is spaced proximally from the proximal end of the cannula tube in the illustration, but may be placed a short distance distal to the very proximal edge of the cannula tube.

Figure 8:
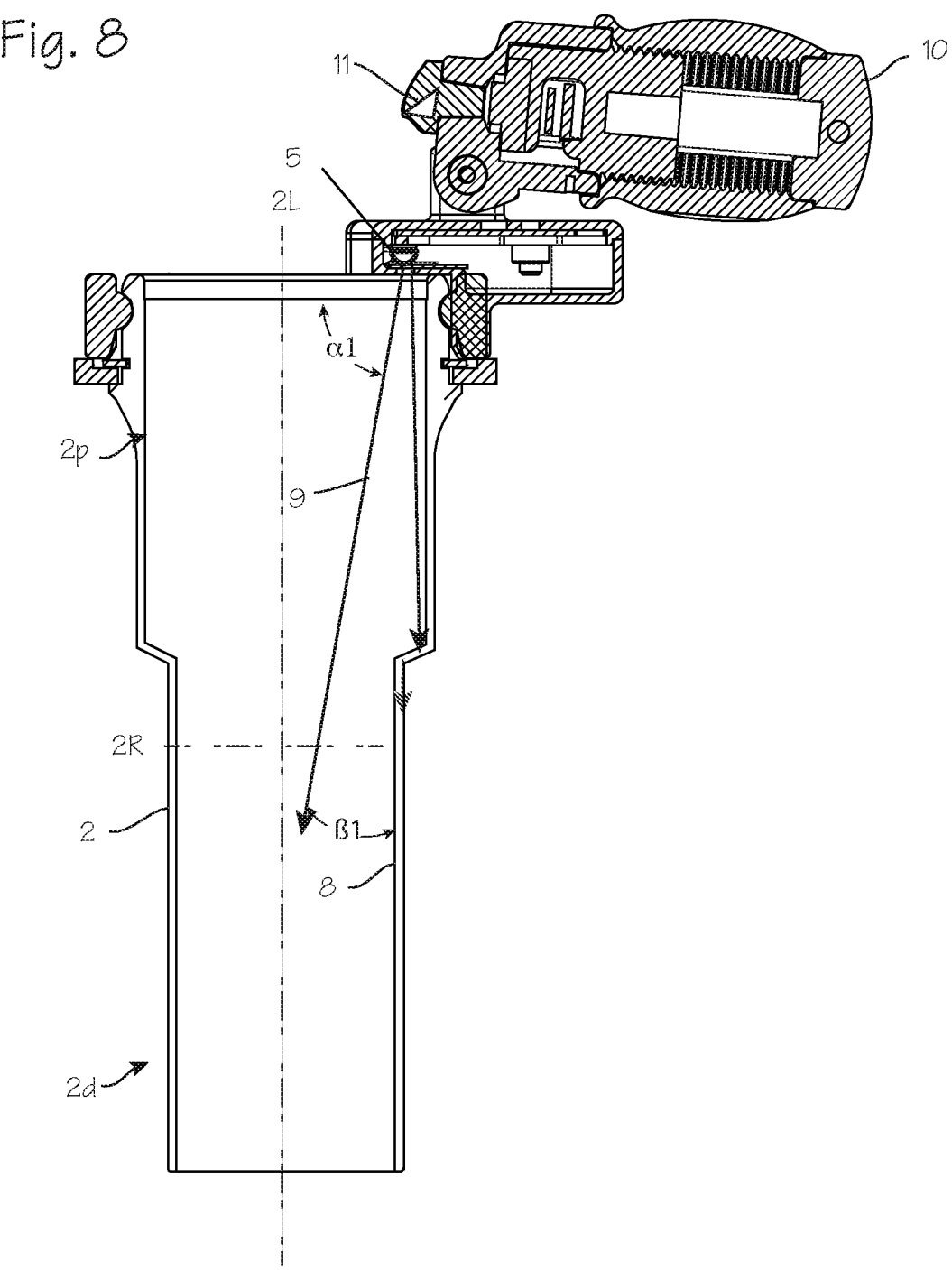
FIG. 8 illustrates a lighted cannula system with a cannula tube of non-uniform diameter, with a proximal light source consisting of two LED's.

FIG. 8 illustrates a lighted cannula system with a cannula tube of non-uniform diameter, with a proximal light source consisting of two LED's 5. FIG. 8 illustrates that the cannula tube of FIG. 5 can be combined with the two-LED light source of FIGS. 1 through 4, to obtain the benefits of the larger proximal lumen in a system using a light source consisting of two LED's. In this embodiment, the two LED's (or two pairs) can be aimed directly distally, with the beam axes parallel to the side wall of the cannula tube, as with FIG. 7, or the beam axes may be angled toward the center of the lumen, as with FIG. 2.

The extreme smoothness of the luminal surface provides for abundant reflection of light from the proximal light sources into the cannula distal end and minimization of shadows cast by tools disposed within the cannula lumen, without the need to resort to more complex tube constructions such as optical fibers embedded in the cannula wall, or optical transmission of light from a light ring into a transparent wall, or construction of the cannula wall to serve as a light guide with rough surface features needed to extract and deliver light at that proximal end of the cannula tube. Though the cannula tube can comprise a transparent material, it is more conveniently made of metal, such as stainless steel or aluminum, which can be made with thinner walls vis-à-vis plastics, and can be sterilized and re-used, and is not subject to abrasion or skiving from abrading tools (more of a concern for spinal surgery). Thus, the cannula tube can consist of an opaque material, preferably metal, without embedded optical fibers or wave guide features. The cannula tube can also consist of a transparent polymer, without embedded optical fibers or wave guide features, though the transparency of the tube is not necessary to obtain the advantages of the inventive features of the cannula system.

Alternatively, the cannula tube can be made of other materials, with a highly reflective material adhered to the luminal walls, which will also provide for good light transmission from the proximal lighting assembly, without embedded optical fibers or wave guide features.

The luminal surface of the cannula tube may be coated to enhance performance in various aspects. The luminal surface may be coated with parylene or other dielectric compound for use in surgeries that require delivery of ablation energy through tools to be inserted into a surgical workspace through the cannula tube. The luminal surface may be coated with a hydrophobic coating, or a lipophobic or oleophobic coating, to minimize build-up of body fluids or irrigation fluids during use.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A cannula system for accessing a target site in the body of a patient, said cannula system comprising:
    a cannula tube having a distal end and a proximal end, and a lumen extending from said proximal end to said distal end, a central longitudinal axis defined by the lumen, and a luminal surface on an inner wall of said cannula tube; and
    a light source disposed proximate the proximal end of the cannula tube, said light source configured to project light into the lumen of the cannula tube; wherein
    the cannula tube comprises an opaque material, non-transmissive to visible light; and
    the luminal surface has an Average Roughness of about 8 micro-inches or smoother.

2. The cannula system of claim 1, wherein:
the cannula tube consists entirely of a material which is non-transmissive to visible light.

3. The cannula system of claim 1, wherein:
the cannula tube comprises a material which is transmissive to visible light and the luminal surface comprises a material which is non-transmissive to visible light.

4. The cannula system of claim 1, wherein:
the light source comprises a plurality of lights disposed on the proximal end of the cannula tube, where the lights are characterized by a main beam axis, and said main beam axis is directed at an angle of about 80° from a radial axis of the cannula tube.

5. The cannula system of claim 1, wherein:
the light source comprises of a plurality of lights disposed on the proximal end of the cannula tube, where the lights are characterized by a main beam axis, and said main beam axis is directed at an angle of about 10° relative to the luminal surface of the cannula tube.

6. The cannula system of claim 1, wherein:
the light source comprises of a plurality of lights disposed on the proximal end of the cannula tube, where the lights are characterized by a main beam axis, and said main beam axis is directed parallel to a portion of the luminal surface on the inner wall of the cannula.

7. The cannula system of claim 1, wherein:
the light source is characterized by a main beam axis, and said beam axis is aimed at an angle of 10 to 30° from a radian of the cannula tube.

8. The cannula system of claim 2, wherein:
the light source consists of two lights, disposed on the proximal end of the cannula tube and separated by a first arc of about 60°, or two pairs of lights, with the pairs separated by a first arc of about 60°.

9. The cannula system of claim 2, wherein:
the inner diameter of the cannula tube proximal end is conical, and the inner diameter of the cannula tube distal end is isodiametric.

10. The cannula system of claim 2, wherein:
the inner diameter of the cannula tube proximal end is isodiametric, and the inner diameter of the cannula tube distal end is isodiametric, and the inner diameter of the cannula tube distal end is smaller than the inner diameter of the cannula tube proximal end, and the cannula tube proximal end and cannula tube distal end are joined by a neck-down portion of the cannula tube.

11. The cannula system of claim 2, wherein:
the inner diameter of the cannula tube, from the proximal end to the distal end, is isodiametric.

12. The cannula system of claim 2, wherein:
the cannula tube consists of metal.

13. The cannula system of claim 2, wherein:
the opaque material of the cannula tube is free of any optical fibers.

14. The cannula system of claim 2, further comprising:
a camera assembly secured to the proximal end of the cannula, with a portion of the camera assembly overhanging the lumen and extending into a cylindrical space defined by the lumen of the cannula tube; wherein
the camera assembly has a distal-most optical surface, and said distal-most optical surface is disposed proximate the proximal end of the cannula tube.

15. The cannula system of claim 8, further comprising:
a camera assembly secured to the proximal end of the cannula, with a portion of the camera assembly overhanging the lumen and extending into a cylindrical space defined by the lumen of the cannula tube; wherein
the camera assembly has a distal-most optical surface, and said distal-most optical surface is disposed proximate the proximal end of the cannula tube; wherein
the camera assembly is radially disposed between the two lights, within the first arc of about 60°.

16. The cannula system of claim 2, further comprising:
an electrically isolating coating on the luminal surface of the cannula tube.

17. The cannula system of claim 2, further comprising:
a hydrophobic coating on the luminal surface of the cannula tube.

18. The cannula system of claim 2, further comprising:
a lipophobic or oleophobic coating on the luminal surface of the cannula tube.

\* \* \* \* \*